United States Patent [19]
Henry et al.

[11] Patent Number: 5,824,665
[45] Date of Patent: *Oct. 20, 1998

[54] REDUCTION OF HAIR GROWTH

[76] Inventors: James Henry, 6776 Wood Duck Ct., Frederick, Md. 21701; Gurpreet Ahluwalia, 8632 Stableview Ct., Gaithersburg, Md. 20852; Douglas Shander, 16112 Howard Landing Dr., Gaithersburg, Md. 20878

[*] Notice: The term of this patent shall not extend beyond the expiration date of Pat. No. 5,652,273.

[21] Appl. No.: 842,054

[22] Filed: Apr. 23, 1997

Related U.S. Application Data

[62] Division of Ser. No. 565,728, Nov. 30, 1995, Pat. No. 5,652,273.

[51] Int. Cl.$^6$ .......................... A61K 31/13; A61K 31/35
[52] U.S. Cl. .......................... 514/143; 514/680; 514/688; 514/468; 514/464; 514/455; 514/311; 514/258
[58] Field of Search ...................... 514/143, 688, 514/680, 468, 464, 455, 311, 258

[56] References Cited

U.S. PATENT DOCUMENTS

| | | |
|---|---|---|
| 3,426,137 | 2/1969 | Philpitt . |
| 4,039,669 | 8/1977 | Beyler et al. . |
| 4,139,638 | 2/1979 | Neri et al. . |
| 4,161,540 | 7/1979 | Neri et al. . |
| 4,191,775 | 3/1980 | Glen . |
| 4,269,831 | 5/1981 | Ferrari et al. . |
| 4,344,941 | 8/1982 | Wiechert et al. . |
| 4,370,315 | 1/1983 | Greff et al. . |
| 4,439,432 | 3/1984 | Peat . |
| 4,508,714 | 4/1985 | Cecic et al. . |
| 4,517,175 | 5/1985 | Iwabuchi et al. . |
| 4,720,489 | 1/1988 | Shander . |
| 4,885,289 | 12/1989 | Breuer et al. . |
| 4,935,231 | 6/1990 | Pigiet . |
| 5,015,470 | 5/1991 | Gibston et al. . |
| 5,095,007 | 3/1992 | Ahluwalia . |
| 5,096,911 | 3/1992 | Ahluwalia et al. . |
| 5,132,293 | 7/1992 | Shander et al. . |
| 5,143,925 | 9/1992 | Shander et al. . |
| 5,189,212 | 2/1993 | Ruenitz . |
| 5,271,942 | 12/1993 | Heverhagen . |
| 5,300,284 | 4/1994 | Wiechers et al. . |
| 5,364,885 | 11/1994 | Ahluwalia et al. . |
| 5,411,991 | 5/1995 | Shander et al. . |
| 5,455,234 | 10/1995 | Ahluwalia et al. . |
| 5,468,476 | 11/1995 | Ahluwalia et al. . |
| 5,474,763 | 12/1995 | Shander et al. . |
| 5,554,608 | 9/1996 | Hentry et al. . |

FOREIGN PATENT DOCUMENTS

| | | |
|---|---|---|
| 0 413 528 A1 | 2/1991 | European Pat. Off. . |
| 0 532 219 A2 | 3/1993 | European Pat. Off. . |
| 0 711 541 A1 | 5/1996 | European Pat. Off. . |
| 1 458 349 | 12/1976 | United Kingdom . |
| Wo 91/04058 | 4/1991 | WIPO . |

OTHER PUBLICATIONS

Sato, "The Hair Cycle and Its Control Mechanism", *Biology and Disease of the Hair* pp. 3–13 (1975).

Goos et al., "An Improved Method for Evaluating Antiandrogens", *Arch. Dermatol. Res.*, 273:333–341 (1982).

Messenger, "The Control of Hair Growth: An Overview", *The Journal of Investigative Dermatology*, 101:4S–9S, supplement, (1993).

Simpson et al., "The Effect of Topically Applied Progesterone on Sebum Excretion Rate", *British Journal of Dermatology*, 100:687–692 (1979).

Harmon et al., "12–0–Tetradecanoylphorbol–13–Acetate Inhibits Human Hair Follicle Growth and Hair Fiber . . . ", *SID Abstracts*, 102:533 (1994).

"Cochlear damage and increased threshold in alphadifluoromethylornithine (DFMO) treated guinea pigs" (abstract only).

Adachi et al., "Human Hair Follicles: Metabolism and Control Mechanisms", *J. Soc. Cosmet. Chem.*, 21, 901–924 (Dec. 9, 1970).

Adachi et al., "Glucose metabolism of growing and resting human hair follicles", *American Journal of Physiology*, vol. 215, No. 5 (Nov. 1968).

Machado de Domenech et al., "Specificity of Hexokinases Towards Some Uncommon Substrates and Inhibitors", *FEBS Letters*, vol. 119, No. 1 (1980).

Johnson et al., "Inhibition of Hexokinase and Protein Kinase Activities of Tumor Cells by a Chloromethyl Ketone Derivative of Lactic Acid", *Biochemistry*, vol. 21, No. 12 (1982).

Colombo et al., "Interaction of Inhibitors with Muscle Phosphofructokinase", *The Journal of Biological Chemistry*, vol. 250, No. 24, Issue of Dec. 25, pp. 9404–9412 (1975).

McCune et al., "Aurintricarboxylie acid is a potent inhibitor of phosphofructokinase", *Biochem. J.*, 259, 925–927 (1989).

Mansour et al., "Affinity Labeling of AMP–ADP Sites in Heart Phosphofructokinaseby 5'–p–Fluorosulfonyl-benzoyl . . . ", *Biochem. and Biophysical Research Communications*, vol. 81, No. 4 (1978).

Avigad et al., "Synthesis of 5–keto–D–Fructose 1,6–Bisphosphate and Some of Its Properties", *Biochimica et Biophysica Acta*, 343, 330–340 (1974).

Kuntz et al., "Phosphoglycerate Kinase from Animal Tissue", *Methods in Enzymology*, vol. 90, 103–110 (1982).

Liu et al., "Synthesis and Study of (z)–3–Chlorophosphoenolpyruvate", *Archives of Biochemistry and Biophysics*, vol. 277, No. 1, Feb. 15, pp. 143–148 (1990).

Wirsching et al., "(E–3–Cyanophosphoenolpyruvate, a New Inhibitor of Phosphoenolpyruvate–Dependent Enzymes", *Biochemistry*, 24, 7602–7606 (1985).

(List continued on next page.)

*Primary Examiner*—Keith D. MacMillan
*Attorney, Agent, or Firm*—Fish & Richardson P.C.

[57] ABSTRACT

A method of reducing hair growth in a mammal includes applying, to an area of skin from which reduced hair growth is desired, a dermatologically acceptable composition containing a suppressor of the metabolic pathway for the conversion of glucose to acetyl-CoA.

20 Claims, 1 Drawing Sheet

OTHER PUBLICATIONS

Spring et al., "Studies on Two High–Affinity Enolase Inhibitors. Reaction with Enolases", *Biochemistry*, vol. 10, No. 25 (1971).

Rose et al., "Inactivation and Labeling of Triose Phosphate Isomerase and Enolase by Glycidol Phosphate", *The Journal of Biological Chemistry*, vol. 244, No. 23, issue of Dec. 10, pp. 6548–6557 (1969).

O'Leary et al., "1–Hydroxycyclopropane Carboxylic Acid Phosphate: A Potent Inhibitor of Enzymes . . . ", *Biochemical and Biophysical Research Communication*, vol. 100, No. 3 (1981).

Blaswanger, "Substrate Specificity of the Pyruvate Dehydrogenase Complex from *Escherichia coli*", *The Journal of Biological Chemistry*, vol. 256, No. 2, issue of Jan. 25, pp. 815–822 (1981).

Furata et al., "Pyruvate Dehydrogenase Complex from Pigeon Breast Muscle", *Methods in Enzymology*, vol. 89, pp. 414–420 (1982).

Waymack et al., "The Effect of Pyruvate Transport Inhibitors on the Regualtion of Pyruvate Dehydrogenase in the Perfused Rat Heart", *Archives of Biochemistry and Biophysics*, vol. 194, No. 1, pp. 258–264 (1979).

Lowe et al., Bromopyruvate as an Active–Site–Directed Inhibitor of the Pyruvate Dehydrogenase Multienzyme Complex from *Escherichia coli*, *Biochemistry*, 23, 91–97 (1984).

Bisswanger, "Fluropyruvate: A Potent Inhibitor of the Bacterial and the Mammalian Pyruvate Dehydrogenase Complex", *Biochemical and Biophysical Research Communications*, vol. 95, No. 2 (1980).

Coe, "Inhibition of Glycolysis in Ascites Tumor Cells Pre-incubated with 2–Deoxy–2–Fluoro–D–Glucose", *Biochim. Biophys. Acta*, 264, 319–327 (1972).

Taylor et al., "Metabolic and Transport Studies with Deoxyfluoro–monosaccharides" *ACS Symposium Series: Biochemistry Involving Carbon–Fluorine Bonds*, pp. 99–116 (1975).

Hanson et al., "Inhibition of Phosphofructokinase by Quinone Methide and α–Methylene Lactone Tumor Inhibitors", *Science*, vol. 168, pp. 378–380 (1970).

Scopes, "3–Phosphoglycerate Kinase of Baker's Yeast", *Methods in Enzymology*, 90:134–138 (1982).

Tielens et al., The Effect of 5–Thioglucose on the Energy Metabolism of Schistosoma Mansoni in Vitro, *Biochemical Pharmacology*, pp. 3369–3373, Abstract only, Sep. 15, 1985.

PCT Search Report. partial copy, PCT/US 96/19102.

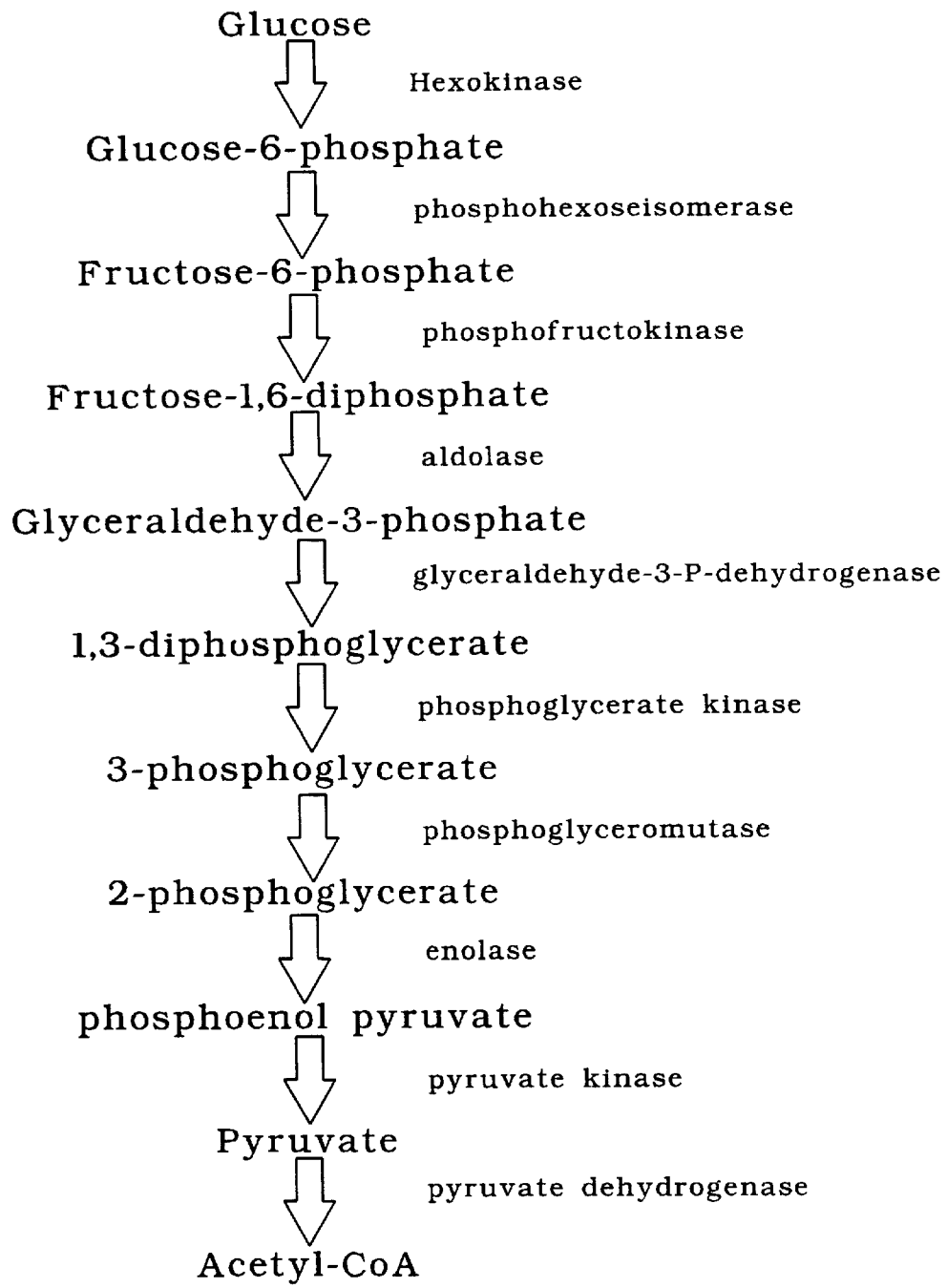

REDUCTION OF HAIR GROWTH

BACKGROUND OF THE INVENTION

This is a divisional of application Ser. No. 08/565,728, filed, Nov. 30, 1995 U.S. Pat. No. 5,652,273.

The invention relates to a method of reducing unwanted hair growth in mammals.

A main function of mammalian hair is to provide environmental protection. However, that function has largely been lost in humans, in whom hair is kept or removed from various parts of the body essentially for cosmetic reasons. For example, it is generally preferred to have hair on the scalp but not on the face.

Various procedures have been employed to remove unwanted hair, including shaving, electrolysis, depilatory creams or lotions, waxing, plucking, and therapeutic anti-androgens. These conventional procedures generally have drawbacks associated with them. Shaving, for instance, can cause nicks and cuts, and can leave a perception of an increase in the rate of hair regrowth. Shaving also can leave an undesirable stubble. Electrolysis, on the other hand, can keep a treated area free of hair for prolonged periods of time, but can be expensive, painful, and sometimes leaves scarring. Depilatory creams, though very effective, typically are not recommended for frequent use due to their high irritancy potential. Waxing and plucking can cause pain, discomfort, and poor removal of short hair. Finally, antiandrogens—which have been used to treat female hirsutism—can have unwanted side effects.

It has previously been disclosed that the rate and character of hair growth can be altered by applying to the skin inhibitors of certain enzymes. These inhibitors include inhibitors of 5-alpha reductase, ornithine decarboxylase, S-adenosylmethionine decarboxylase, gamma-glutamyl transpeptidase, and transglutaminase. See, for example, Breuer et al., U.S. Pat. No. 4,885,289; Shander, U.S. Pat. No. 4,720,489; Ahluwalia, U.S. Pat. No. 5,095,007; Ahluwalia et. al., U.S. Pat. No. 5,096,911; Shander et al., U.S. Pat. No. 5,132,293; and Shander et al., U.S. Pat. No. 5,143,925.

Metabolism of glucose to acetyl-CoA is carried out by a series of enzymes, with some enzymes performing a more regulatory (i.e., rate limiting) role than others. The FIGURE illustrates the metabolic pathway for the conversion of glucose to acetyl-CoA.

Referring to the FIGURE, the first enzyme in the series is hexokinase, which converts glucose to glucose-6-phosphate. The enzyme phosphohexoseisomerase then converts the glucose-6-phosphate to fructose-6-phosphate, which in turn is converted by phosphofructokinase to fructose-1,6-diphosphate. The enzyme aldolase then converts the fructose-1,6-diphosphate to glyceraldehyde-3-phosphate, which in turn is converted by glyceraldehyde-3-P-dehydrogenase to 1,3-diphosphoglycerate. The enzyme phosphoglycerate kinase then converts the 1,3-diphosphoglycerate to 3-phosphoglycerate, which in turn is converted by the enzyme phosphoglyceromutase to 2-phosphoglycerate. The enzyme enolase then converts the 2-4-phosphoglycerate to phospho(enol)pyruvate, which in turn is converted by pyruvate kinase to pyruvate. Pyruvate, finally, is converted by pyruvate dehydrogenase to acetyl-CoA.

The conversion of glucose to acetyl-CoA occurs inside the cell. Thus, for the conversion to occur glucose must be transported into the cell. The metabolic pathway for the conversion of glucose to acetyl-CoA, as used herein, includes the transport of glucose into the cell.

It has now been found that unwanted mammalian (including human) hair growth—particularly androgen stimulated hair growth—can be reduced by applying to the skin a dermatologically acceptable composition including a compound that suppresses the metabolic pathway for the conversion of glucose to acetyl-CoA in an amount effective to reduce hair growth. The unwanted hair growth which is reduced may be normal hair growth, or hair growth that results from an abnormal or diseased condition.

Compounds that suppress the metabolic pathway for the conversion of glucose to acetyl-CoA include inhibitors of the enzymes involved in the metabolic pathway and inhibitors of glucose transport into the cell. Preferably, the metabolic pathway is suppressed using an inhibitor of hexokinase, phosphofructokinase, pyruvate dehydrogenase, or glucose transport.

Examples of inhibitors of hexokinase include 6-amino-6-deoxy-glucose, N-acetyl-β-D-mannosamine, D-mannosamine, and N-α-(p-tosyl)-L-lysine chloromethyl ketone. See de Domenech, FEBS Letters 119:174–76, 1980; and Johnson, Biochemistry 21:2984–89, 1982.

Examples of inhibitors of phosphofructokinase include phosphoglycerate, quinone methides (e.g., taxodone, taxodione), α-methylene lactones (e.g., euparotin acetate eupacunin, vernolepin), argaric acid, quinaldic acid, and 5'-p-flurosuflonylbenzoyl adenosine. See Colombo, J. Biol. Chem., 250:9404–12, 1975; Hanson, Science 163:378–80, 1970; McCune, Biochem. J., 259:925–27, 1989; and Mansour, Biochem. Biophys. Res. Commun., 81:1370–76, 1978.

Examples of inhibitors of aldose include 5-keto-D-fructose and 5-keto-D-fructose-1,6-bisphosphate. See Avigad, Biochem. Biophys. Acta, 343:330–40, 1974.

Examples of inhibitors of phosphoglycerate kinase include Mg-phosphoglycerate and 2,3-diphosphoglycerate. See Scopes, Methods in Enzymology, 90:134–38, 1982; and Gunter, Methods in Enzymology, 90:103–10, 1982.

Examples of inhibitors of enolase include 3(trans)-chlorophosphoenolpyruvate, 3(cis)-cyanophosphoenolpyruvate, D-tartronate semialdehyde phosphate, aminoenolpyruvate, D-glycidol phosphate, and L-glycidol phosphate. See Liu, Arch. Biochem. Biophys. 277:143–48, 1990; Wirsching, Biochemistry 24:7602–06, 1985; Spring, Biochemistry, 10:4655–60, 1971; and Rose, J. Biol. Chem., 244:6548–57, 1969.

Examples of inhibitors of pyruvate kinase include hydroxy-1-cyclopropanecarboxylic acid and D(-)3-phosphoglyceric acid. See O'Leary, Biochem. Biophys. Res. Commun. 100:1320–25, 1981.

Examples of inhibitors of pyruvate dehydrogenase include glyoxylate, hydroxypyruvate, kynurenate, xanthurenate, α-cyano-4-hydroxycinnamic acid, bromopyruvic acid, and fluropyruvic acid. See Bisswanger, J. Biol. Chem. 256:815–22, 1981; Furuta, Methods in Enzymology, 89:414–20, 1982; Waymack, Arch. Biochem. Biophys., 194:258–64, 1979; Lowe, Biochemistry, 23:91–97, 1984; and Bisswanger, Biochem. Biophys. Res. Commun. 95:513–19, 1980.

Examples of inhibitors of glucose transport include phloretin, 5-thio-D-glucose, 2-deoxyglucose, 2-deoxy-2-fluoro-D-glucose, 3-deoxyglucose, and 3-deoxy-3-fluoro-D-glucose. See Coe, Biochim Biophys Acta, 264:319–27, 1972; and Taylor, ACS Symposium Series, 170th meeting of ACS, 99–116, 1975.

The hair growth reducing compound is incorporated in a non-toxic dermatologically acceptable topical composition which preferably includes a vehicle or carrier which is adapted to be spread upon the skin. Examples of suitable vehicles are acetone, alcohols, or a cream, lotion, or gel which can effectively deliver the active compound. One such vehicle is disclosed in co-pending application PCT/US93/0506A. In addition, a penetration enhancer may be added to the vehicle to further enhance the effectiveness of the formulation.

The concentration of the hair growth inhibiting compound in the composition may be varied over a wide range up to a saturated solution, preferably from 0.1% to 30% by weight or even more; the reduction of hair growth increases as the amount of compound applied increases per unit area of skin. The maximum amount effectively applied is limited only by the rate at which the hair growth inhibiting compound penetrates the skin. Generally, the effective amounts range from 10 to 3000 micrograms or more per square centimeter of skin.

The composition should be topically applied to a selected area of the body from which it is desired to reduce hair growth. For example, the composition can be applied to the face, particularly to the beard area of the face, i.e., the cheek, neck, upper lip, and chin. The composition can also be applied to the legs, arms, torso or armpits. The composition is particularly suitable for reducing the growth of unwanted hair in women suffering from hirsutism or other conditions. In humans, the composition should be applied once or twice a day, or even more frequently, for at least three months to achieve a perceived reduction in hair growth. Reduction in hair growth is demonstrated when the frequency or hair removal is reduced, or the subject perceives less hair on the treated site, or quantitatively, when the weight of hair removed by shaving (i.e., hair mass) is reduced.

Male intact Golden Syrian hamsters are considered acceptable models for human beard hair growth in that they display oval shaped flank organs, one on each side, each about 8 mm in major diameter, which grow thick black and coarse hair similar to human beard hair. These organs produce hair in response to androgens in the hamster. To evaluate the effectiveness of a composition including a hair growth reducing compound, the flank organs of each of a group of hamsters are depilated by applying a thioglycolate based chemical depilatory (Surgex); alternatively, hair were removed by shaving the flank organs prior to topical treatments. To one organ of each animal 10 $\mu$l of vehicle alone once a day is applied, while to the other organ of each animal an equal amount of vehicle containing a hair growth reducing compound is applied. After thirteen applications (one application per day for five days a week), the flank organs are shaved and the amount of recovered hair (hair mass) from each is weighed. Percent-reduction of hair growth is calculated by subtracting the hair mass (mg) value of the test compound treated side from the hair mass value of the vehicle treated side; the delta value obtained is then divided by the hair mass value of the vehicle treated side, and the resultant number is multiplied by 100.

The above-described assay will be referred to herein as the "Golden Syrian hamster" assay. Preferred compositions provide an inhibition in hair growth of at least about 20%, more preferably at least about 40%, and most preferably at least about 60% when tested in the Golden Syrian hamster assay. A number of compositions were tested in the Golden Syrian hamster assay; the results are provided in the Table.

TABLE

| Compound | Vehicle | pH | Hair Mass (mg) ± SEM Treated | Untreated | % Inhibition |
|---|---|---|---|---|---|
| N-α-(p-Tosyl)-L-lysine chloromethyl ketone | A | 5.0 | 0.48 ± .11 | 2.34 ± .26 | 81 ± 4 |
| Quinaldic Acid | A | 4.5 | 0.62 ± .08 | 2.10 ± .20 | 69 ± 4 |
| Mannosamine | A | 6.0 | 0.71 ± .13 | 2.27 ± .22 | 68 ± 6 |
| Phosphogylcolic acid | B | 3.0 | 0.57 ± .09 | 1.80 ± .28 | 66 ± 5 |
| N-Acetyl-β-D-mannosamine | A | 6.0 | 0.79 ± .15 | 2.32 ± .13 | 65 ± 7 |
| Kynurenic acid | A | 8.0 | 0.98 ± .09 | 2.89 ± .28 | 64 ± 4 |
| Xanthurenic acid | C | 8.5 | 1.26 ± .13 | 3.40 ± .16 | 59 ± 4 |
| 5'-p-Flurosuflonylbenzoyl adenosine | A | 7.0 | 0.74 ± .05 | 1.97 ± .24 | 60 ± 3 |
| 6-Amino-6-deoxy glucose | A | 8.0 | 0.77 ± .15 | 1.90 ± .18 | 59 ± 6 |
| Bromopyruvic acid | A | 3.5 | 1.10 ± .11 | 2.75 ± .35 | 58 ± 6 |
| Phenylpyruvic acid | D | 7.5 | 0.92 ± .21 | 4.95 ± .15 | 54 ± 10 |
| Argaric acid | E | 4.0 | 0.97 ± .14 | 2.02 ± .19 | 52 ± 4 |
| α-Cyano-4-hydroxycinnamic acid | F | 7.0 | 0.87 ± .34 | 1.64 ± .19 | 49 ± 17 |
| 5-Thio-D-glucose | A | 6.0 | 1.32 ± .20 | 2.53 ± .14 | 49 ± 6 |
| 3-Fluoropyruvic acid | A | 7.0 | 1.14 ± .09 | 2.00 ± .17 | 40 ± 5 |
| 2-Deoxyglucose | A | 5.0 | 0.96 ± .16 | 1.55 ± .18 | 38 ± 7 |
| Phloretin | G | 7.0 | 1.34 ± .11 | 2.15 ± .14 | 35 ± 7 |
| 1-Hydroxy-1-cyclopropanecarboxylic acid | A | 6.0 | 1.80 ± .20 | 2.28 ± .12 | 22 ± 9 |
| D(−)3-Phosphoglyceric acid | H | 4.5 | 2.27 ± .22 | 2.89 ± .12 | 21 ± 7 |

BRIEF DESCRIPTION OF THE DRAWING

The FIGURE is a flow chart describing metabolic pathways of the conversion of glucose to acetyl-CoA.

SUMMARY OF THE INVENTION

All compounds were tested at a 10% concentration in the following carriers (vehicles), except for 5'-p-fluorosulfonylbenzoyl adenosine, xanthurenic acid and phloretin which-were at 4.4%, 7.5%, and 15.0% respectively.

| Vehicle A: | 68% Water, 16% ethanol, 5% propylene glycol, 5% dipropylene glycol, A% benzyl alcohol, and 2% propylene carbonate. |
| Vehicle B: | 80% Ethanol, 10% dipropylene glycol, and 10% water. |
| Vehicle C: | 95% Water, and 5% DMSO. |
| Vehicle D: | 80% Water, 10% ethanol, and 10% propylene glycol. |
| Vehicle E: | 50% DMSO, 40% ethanol, 8.75% water, 1% propylene glycol dipelargonate (Emerest 2388), and 0.25% propylene glycol. |

-continued

All compounds were tested at a 10% concentration in the following carriers (vehicles), except for 5'-p-fluorosulfonylbenzoyl adenosine, xanthurenic acid and phloretin which-were at 4.4%, 7.5%, and 15.0% respectively.

| Vehicle F: | 80% Ethanol, 17.5% water, 2% propylene glycol dipelargonate (Emerest 2388) and 0.5% propylene glycol. |
|---|---|
| Vehicle G: | 80% Ethanol, 10% propylene glycol, and 10% water. |
| Vehicle H: | 90% Water, and 10% propylene glycol. |

The activity of two target enzymes (phosphofructokinase and hexokinase) was determined in hair follicle extracts in the presence or absence of select enzyme inhibitors.

Measurement of Phosphofructokinase Activity in Hair Follicle Extracts

Hair follicles from hamster flank organs were excised and an enzyme extract was prepared in a buffered mixture containing 75 mM Tris-HCL, 3 mM $MgCl_2$, and 15 mM $(NH_4)_2SO_4$, pH 7.5, using a sonication device. The follicle extracts were passed through a 10,000 molecular weight cut off filter by centrifugation at 12,000 x g. The unfiltered extract was transferred to another filter and a 100 ul aliquot of the magnesium buffer was added. The sample was centrifuged again under similar conditions. This procedure was repeated two additional times.

The washed extract was removed from the insert cup and assayed for phosphofructokinase activity according to the following procedure. The extract was mixed with a solution containing 2.0 ml of the magnesium buffer, 0.1 ml of fructose 6-phosphate (30 mM), 0.1 ml ATP (15 mM), 0.1 ml NADH (1.5 mM), 0.3 ml of mercatopethanol (0.1M), 0.3 ml an auxiliary enzyme mixture made up of aldose (10 units/ml), triosephosphate isomerase (8 units/ml), and α-glycerophosphate dehydrogenae (4 units/ml) in 25 mM Tris-HCI (pH 7.5). The reaction mixture was incubated at 28 C. for 5 min. A 0.1 ml aliquot of hamster hair follicle extract was added to initiate the enzyme reaction. Change in absorbance at UV 340 nm was used to determine the enzyme activity. The assay was found to be linear from 0–1.1 mg protein/ml of reaction mixture.

The enzyme inhibitor agaric acid caused a 76% inhibition of the hair follicle phosphofructokinase activity at a concentration of 0.15 mM. The inhibitor phosphoglycolic acid inhibited the enzyme by 45% at a concentration of 0.9 mM.

Measurement of the Hexokinase Activity was Performed as Follows

The enzyme hexokinase was extracted from the hamster hair follicles in a buffer containing Tris-HCL (0.25M, pH 8.1), 1.5 mM EDTA and 5.0 mM $MgCl_2$. The extract was prepared in a manner similar to as described above for phosphofructokinase. The following reagents were mixed together and the change in absorbance at 340 nM was monitored to determine enzyme activity—0.5 ml of the Tris buffer, 0.1 ml ATP (5 mM), 0.1 ml phospho(enol)pyruvate and NADH (0.75 mM and 0.2 mM respectively), 0.1 ml of the follicle extract. The assay was found to be linear from 0–5.8 mg protein/ml follicle extract.

The enzyme inhibitors mannosamine, N-acetyl-β-D-mannosamine, and N-α-(p-tosyl)lysine-chloromethyl ketone caused complete inhibition (100%) of the hair follicle hexokinase activity at a concentration of 1 mM. The inhibitor 6-amino-6-deoxyglucose inhibited the enzyme by 46% at the same concentration, i.e., 1 mM.

It will be appreciated by those skilled in the art that the invention can be performed within a wide range of equivalent parameters of composition and conditions without departing from the spirit or scope of the invention or of any embodiment thereof.

We claim:

1. A method of reducing mammalian hair growth which comprises selecting an area of skin from which reduced hair growth is desired; and applying to said area of skin a dermatologically acceptable composition comprising an inhibitor of phosphofructokinase in an amount effective to inhibit hair growth.

2. The method of claim 1, wherein said inhibitor comprises phosphoglycerate.

3. The method of claim 1, wherein said inhibitor comprises a quinone methide.

4. The method of claim 3, wherein said quinone methide comprises taxodone.

5. The method of claim 3, wherein said quinone methide comprises taxodione.

6. The method of claim 1, wherein said inhibitor comprises α-methylene lactone.

7. The method of claim 6, wherein said α-methylene lactose comprises euparotin acetate.

8. The method of claim 6, wherein said α-methylene lactose comprises eupacunin.

9. The method of claim 6, wherein said α-methylene lactose comprises vernolepin.

10. The method of claim 1, wherein said inhibitor comprises argaric acid.

11. The method of claim 1, wherein said inhibitor comprises quinaldic acid.

12. The method of claim 1, wherein said inhibitor comprises 5'-p-flurosuflonylbenzoyl adenosine.

13. The method of claim 1, wherein the concentration of said suppressor in said composition is between 1% and 30% by weight.

14. The method of claim 1, wherein the composition provides a reduction in hair growth of at least 20% when tested in the Golden Syrian hamster assay.

15. The method of claim 1, wherein the composition provides a reduction in hair growth of at least 50% when tested in the Golden Syrian hamster assay.

16. The method of claim 1, wherein the composition provides a reduction in hair growth of at least 70% when tested in the Golden Syrian hamster assay.

17. The method of claim 1, wherein the suppressor is applied to the skin in an amount of from 10 to 3000 micrograms of said inhibitor per square centimeter of skin.

18. The method of claim 1, wherein said mammal is a human.

19. The method of claim 18, wherein said area of skin is on the face of the human.

20. The method of claim 19, wherein said human is a woman suffering from hirsutism.

* * * * *